US008884092B2

(12) United States Patent
Rauch et al.

(10) Patent No.: US 8,884,092 B2
(45) Date of Patent: Nov. 11, 2014

(54) SIMULATED MOVING BED SYSTEMS FOR SEPARATION OF PARA-XYLENE AND PROCESSES FOR DETERMINING PUMP-AROUND PROFILES OF THE SIMULATED MOVING BED SYSTEMS

(71) Applicant: UOP LLC, Des Plaines, IL (US)

(72) Inventors: Andrea L. Rauch, Alsip, IL (US); Richard C. Murray, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/676,778

(22) Filed: Nov. 14, 2012

(65) Prior Publication Data

US 2013/0158332 A1  Jun. 20, 2013

Related U.S. Application Data

(60) Provisional application No. 61/577,213, filed on Dec. 19, 2011.

(51) Int. Cl.
*C07C 7/12* (2006.01)
*C07C 15/08* (2006.01)
*G01N 21/65* (2006.01)
*G01J 3/44* (2006.01)

(52) U.S. Cl.
CPC ............... *G01J 3/4412* (2013.01); *C07C 7/12* (2013.01); *G01N 21/65* (2013.01)
USPC ............................ 585/821; 585/822; 585/823

(58) Field of Classification Search
None
See application file for complete search history.

(56) References Cited

U.S. PATENT DOCUMENTS

| 5,457,260 | A | 10/1995 | Holt |
| 5,470,482 | A | 11/1995 | Holt |
| 5,596,196 | A | 1/1997 | Cooper |
| 5,684,580 | A | 11/1997 | Cooper |
| 6,162,644 | A | 12/2000 | Choi |
| 2009/0105515 | A1* | 4/2009 | Winter et al. ................. 585/822 |
| 2011/0198500 | A1* | 8/2011 | Hotier et al. ................. 250/343 |

OTHER PUBLICATIONS

Brown, Raman Process Analyzer for in-situ and Real-Time Measurement of Chemical Composition; ISA—The Instrumentation Systems and Automation Society, presented at ISA AD 2007 Analysis Division Symposium, http://www.isa.org.
Marteau, Remote Raman Spectroscopy for Process Control; Vibrational Spectroscopy, vol. 9, Issue 1, May 1995, pp. 101-109.

* cited by examiner

*Primary Examiner* — Tam M Nguyen
(74) *Attorney, Agent, or Firm* — Mark R Willis

(57) ABSTRACT

Embodiments of simulated moving bed systems for separating a preferentially adsorbed component from a feed stream and processes for determining a pump-around profile of the simulated moving bed systems are provided. The process comprises the steps of rotating a rotary valve to a first valve position to direct the feed stream to a first adsorbent sub-bed. An intermediate stream between two adsorbent sub-beds in direct fluid communication with each other is irradiated with laser light that is directed from a probe of a Raman system positioned for inline sampling of the intermediate stream. Scattered light from the irradiated intermediate stream is collected with the probe. A spectrum of the scattered light is generated with the Raman system to determine concentrations of the preferentially adsorbed component and one or more other components in the intermediate stream.

14 Claims, 6 Drawing Sheets

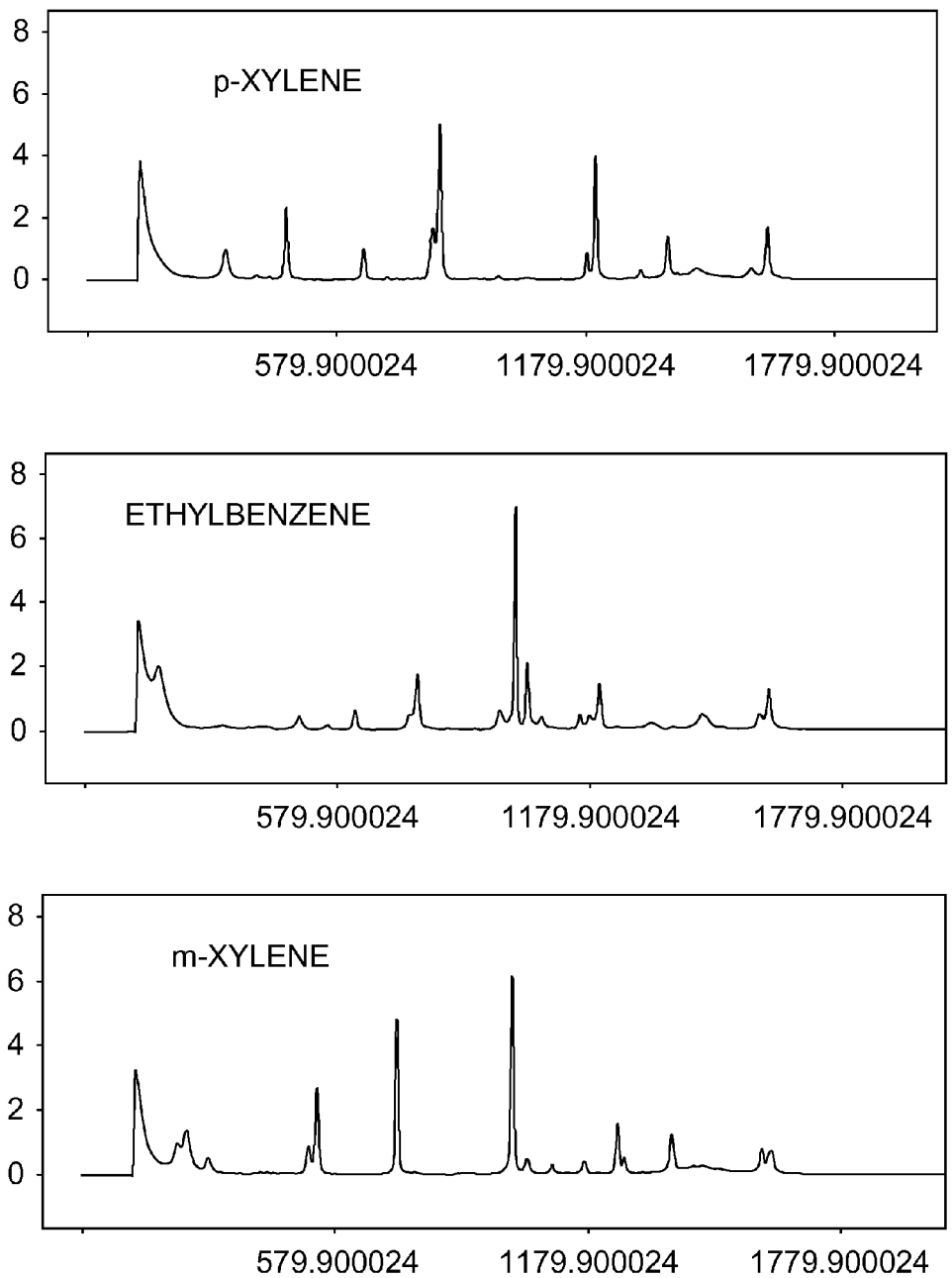

SIMULATED MOVING BED SYSTEMS FOR SEPARATION OF PARA-XYLENE AND PROCESSES FOR DETERMINING PUMP-AROUND PROFILES OF THE SIMULATED MOVING BED SYSTEMS

CROSS-REFERENCE TO RELATED APPLICATION

This application claims the benefit of U.S. Provisional Application No. 61/577,213 filed on Dec. 19, 2011.

FIELD OF THE INVENTION

The present invention relates generally to systems and processes for separating a preferentially adsorbed component from a mixture of other components, and more particularly relates to simulated moving bed systems for separating para-xylene from a mixture of other xylene isomers and hydrocarbons and processes for determining the pump-around profiles of the simulated moving bed systems.

BACKGROUND OF THE INVENTION

Continuous separation processes are commonly used for the selective adsorption of para-xylene from a mixture of $C_8$ aromatics. Generally, the processes use a solid adsorbent that preferably retains the para-xylene in order to separate the para-xylene from the rest of the mixture. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds or modules. The shift in the locations of the liquid input and output in the direction of the fluid flow through the bed simulates the movement of the solid adsorbent in the opposite direction. Moving the locations of the liquid input and output is accomplished by a fluid tracking device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time or hold period, the rotary valve advances one index to the next valve position and redirects the liquid inputs and outputs to the distributors immediately adjacent and downstream of the previously used distributors. Each advancement of the rotary valve to the next valve position is generally called a valve step, and the completion of all the valve steps is called a valve cycle. In one commercial process, the step time is uniform for each of the valve steps in a valve cycle, and is generally about 60 seconds or so. A typical process contains 24 adsorbent sub-beds, 24 distributors located between the 24 adsorbent sub beds, two liquid input lines, two liquid output lines, and associated flush lines.

The principle liquid inputs and outputs of the adsorbent system consists of four streams, which are the feed, the extract, the raffinate, and the desorbent. Each stream flows into or out of the adsorbent system at a particular flow rate, and each rate is independently controlled. The feed, which is introduced to the adsorbent system, contains the para-xylene that is to be separated from the other components in the feed stream. The desorbent, which is introduced to the adsorbent system, contains a liquid capable of displacing feed components from the adsorbent. The extract, which is withdrawn from the adsorbent system, contains the separated para-xylene, which was selectively adsorbed by the adsorbent, and the desorbent liquid. The raffinate, which is withdrawn from the adsorbent system, contains other $C_8$ aromatic components of the feed that are less selectively adsorbed by the adsorbent, and desorbent liquid. There also may be associated flush streams introduced to and withdrawn from the adsorbent system. The four principal streams are spaced strategically throughout the adsorbent system and divide the sub-beds into four zones, each of which performs a different function.

Zone I contains the adsorbent sub-beds located between the feed input and the raffinate output, and the selective adsorption of the para-xylene takes place in this zone. Zone II contains the adsorbent sub-beds located between the extract output and the feed input, and the desorption of components other than the para-xylene takes place in this zone. Zone III contains the adsorbent sub-beds located between the desorbent input and the extract output, and the para-xylene is desorbed in this zone. Finally, Zone IV contains the adsorbent sub-beds located between the raffinate output and the desorbent input. The purpose of zone IV is to prevent the contamination of the para-xylene with other components.

A common practice in the industry is to determine the compositional profile of the para-xylene simulated moving bed separation process either by on-line gas chromatography analysis, or by off-line laboratory analysis. The on-line gas chromatography analysis typically requires about 10 minutes per analysis, which is considerably greater than the usual step time of the rotary valve. Therefore, only selected valve positions can be sampled and analyzed. Generally, only Zone II near the extract output and Zone IV near the desorbent input are sampled and analyzed. The data provided by this on-line gas chromatography procedure is useful for detecting some process upsets, but unfortunately analyzing the composition of only two valve positions provides limited information regarding the performance of the separation process and is only minimally useful for precise separation process control.

A more thorough determination of the compositional profile of the para-xylene simulated moving bed separation process is accomplished using off-line laboratory gas chromatography analysis to determine the values of the concentrations of the components in the samples for each valve position in a valve cycle. The measured concentrations are then plotted versus their relative valve positions to form what is generally called a pump-around profile. Using the pump-around profile, the recovery purity of the para-xylene can be calculated and the degree of optimization of the separation may be assessed. From this, for example, needed changes in the step time and/or liquid stream flow rates may be determined and implemented. The drawbacks to assessing the separation process in this fashion are the time delay between sampling and delivery of the analytical results, where the latter are used to determine whether or what process changes should be made; the labor involved to manually collect the stream samples; and the personal exposure of the operator manually collecting the stream samples from the process. Since the analysis is performed off-line, the time delay may be from one to several days long and can lead to plant disruption. Because of these drawbacks, refiners generally only perform this procedure about once every six months or if there is a problem with the separation process.

Accordingly, it is desirable to provide systems for the separation of para-xylene from other hydrocarbon components and processes for determining the pump-around profile of these systems to provide rapid and frequent compositional profiles with low system maintenance, requiring minimal operator time and labor, and without plant disruption. Furthermore, other desirable features and characteristics of the present invention will become apparent from the subsequent detailed description of the invention in the appended claims, taken in conjunction with the accompanying drawings and this background of the invention.

SUMMARY OF THE INVENTION

Simulated moving bed systems for separating para-xylene from a feed mixture of $C_8$ aromatics and processes for determining the pump-around profiles of these simulated moving bed systems are provided herein. In accordance with an exemplary embodiment, a process for determining a pump-around profile of a simulated moving bed system having a plurality of adsorbent sub-beds in fluid communication with each other and with a rotary valve for separation of para-xylene from a feed stream comprising para-xylene and one or more other $C_8$ aromatics is provided. The process comprises the steps of rotating the rotary valve to a first valve position to direct the feed stream to a first adsorbent sub-bed of the plurality of adsorbent sub-beds. An intermediate stream between two of the adsorbent sub-beds in direct fluid communication with each other is irradiated with laser light that is directed from a probe of a Raman system positioned for inline sampling of the intermediate stream. Scattered light from the irradiated intermediate stream is collected with the probe. A spectrum of the scattered light is generated with the Raman system to assess concentrations of one or more of para-xylene and other components in the intermediate stream, including in one approach one or more other $C_8$ aromatics in the intermediate stream.

In accordance with another exemplary embodiment, a simulated moving bed system for separating para-xylene from a feed stream comprising para-xylene and one or more other $C_8$ aromatics is provided. The system comprises a plurality of adsorbent sub-beds in fluid communication with each other. The adsorbent sub-beds comprise two adsorbent sub-beds in direct fluid communication with each other via an intermediate stream. A rotary valve is in fluid communication with each of the plurality of adsorbent sub-beds and is configured to rotate to a plurality of valve positions that each direct the feed stream to a different one of the plurality of adsorbent sub-beds. A Raman system comprises a probe and a Raman spectrophotometer. The probe is positioned for inline sampling of the intermediate stream and is configured to irradiate the intermediate stream with laser light and to collect scattered light from the irradiated intermediate stream. The Raman spectrophotometer is cooperatively configured with the probe to generate a spectrum of the scattered light to determine concentrations of one or more of para-xylene and one or more other components, including in one approach one or more other $C_8$ aromatics, in the intermediate stream produced during the rotary valve being in at least one of the valve positions.

BRIEF DESCRIPTION OF THE DRAWINGS

Embodiments of the present invention will hereinafter be described in conjunction with the following drawing figures, wherein like numerals denote like elements, and wherein:

FIGS. 4a-4b include Raman spectra of para-xylene, meta-xylene, ortho-xylene, ethylbenzene, para-diethylbenzene, and n-hexane.

DETAILED DESCRIPTION

Figure 1:
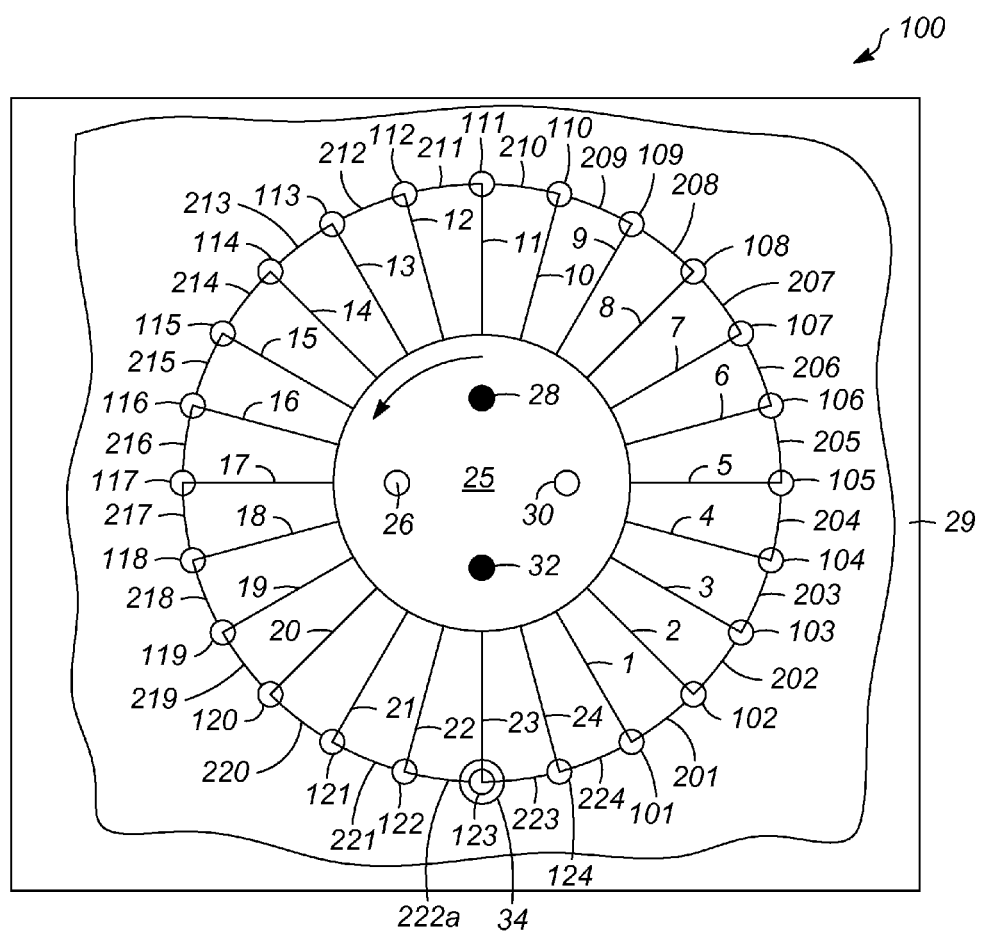
FIG. 1 schematically illustrates a tear away plan view of a simulated moving bed system in accordance with an exemplary embodiment.

The following Detailed Description is merely exemplary in nature and is not intended to limit the invention or the application and uses of the invention. Furthermore, there is no intention to be bound by any theory presented in the preceding Description of Related Art or the following Detailed Description.

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention, without so limiting it, is the recovery of para-xylene and/or meta-xylene from mixtures of $C_8$ aromatics.

The invention normally is employed in an adsorptive separation process which simulates countercurrent movement of the adsorbent and surrounding liquid as described above, but it may also be practiced in a concurrent continuous process, like that disclosed in U.S. Pat. Nos. 4,402,832 and 4,478,721. Processes for separating components of a feed stream are discussed in Chapter 10.3 of the Handbook of Petroleum Refining Processes, 2d Edition at pages 10.45-10.81, which is incorporated by reference herein.

Various embodiments contemplated herein relate to simulated moving bed systems for separating one or more components from a feed stream. One approach relates to the separation of para-xylene from a feed stream containing a hydrocarbon mixture and processes for determining a pump-around profile of the simulated moving bed systems. Another approach relates to the separation of meta-xylene from a feed stream containing a hydrocarbon mixture and processes for determining a pump-around profile of the simulated moving bed system. Other separations using simulated moving bed technologies and processes for determining a pump-around profile of the simulated moving bed systems are also contemplated herein. The simulated moving bed system has a plurality of adsorbent sub-beds in fluid communication with each other and with a rotary valve for separating a preferentially adsorbed component from one or more non-preferentially adsorbed components of the feed stream, for example the separation of para-xylene from the feed stream comprising para-xylene and one or more other $C_8$ aromatics. Turning to more of the particulars, and with reference to a system for separating para-xylene from the feed stream comprising para-xylene and one or more other $C_8$ aromatics, the $C_8$ aromatics usually are derived within an aromatics complex by the catalytic reforming of naptha followed by extraction and fractionation, or by transalkylation or isomerization of aromatics-rich streams in such complexes. The $C_8$ aromatics typically comprise a mixture of xylene isomers, including para-xylene, ortho-xylene, and meta-xylene and ethylbenzene. The feed stream may also include other components. The Raman system includes a probe operatively coupled to a Raman spectrophotometer, by, for example, an optical fiber optic cable or cables. Without interrupting, or altering the volume of, the process stream of the simulated moving bed system, the probe is positioned for inline sampling of an intermediate stream that is between two of the adsorbent sub-beds that are in direct fluid communication with each other. In an exemplary embodiment, a computer operatively interfaces with the Raman spectrophotometer, and a controller operatively interfaces with the rotary valve and the computer. In response to the rotary valve rotating an index to a particular valve position to reposition the feed stream, the controller generates a signal to the computer which triggers the Raman system to begin analyzing the intermediate stream. Preferably, an idle time between when the rotary valve indexes and the Raman system begins analyzing the intermediate stream is used to ensure an accurate assessment of the concentration of the intermediate stream produced during the rotary valve being in a particular valve position. The intermediate stream is irradiated with laser light directed from the probe preferably in the visible, near infrared, or near ultraviolet range, and most preferably in the near infrared due to fewer issues with fluorescence. Preferably, the Raman spectrophotometer is configured to have variation in laser light intensity of about +/−5%, and more preferably of about +/−3% or less. The laser light impinges upon and excites molecules of the components in the intermediate stream from their ground state to a virtual energy state. When the molecules begin to relax, they emit photons and return to a different rotational or vibrational state. The difference in energy between the original state and the new state leads to a shift in the emitted photons' frequencies away from the excitation wavelength. This emitted light, which is referred to as scattered light and is characteristic of the composition of the intermediate stream, is collected by the probe. The Raman system generates a spectrum of the scattered light. Since the intermediate stream contains various amounts of para-xylene and one or more other components, including in one approach the one or more other $C_8$ aromatics from the feed stream based on the valve position, the spectrum is typically a composite of all of these components. It should be noted that the amount or concentration of a component within an intermediate stream can be zero at a particular valve position. An algorithm that correlates the concentrations of the components to the spectrum is preferably used to analyze the spectrum and to calculate the concentrations of the components. The concentration of each of the components may then be graphically represented for that particular valve position. In an exemplary embodiment, the Raman spectrophotometer in combination with a controller, computer and the algorithm are used to automatically generate and graphically represent the concentrations of each of the components in the intermediate stream for each valve position for a full valve cycle to generate a pump-around profile. This process may run continuously to provide ongoing pump-around profiles of the simulated moving bed system. Thus, the pump-around profiles of the system can be provided with rapid and frequent analytical results. Furthermore, the process can be fully automated requiring little or no maintenance and essentially no operator time and labor for generating the pump-around profiles. Moreover, the probe is positioned for inline sampling of the intermediate stream to provide information similar to the manual sampling procedure but without increasing the process stream volume or disrupting production.

Figure 2:
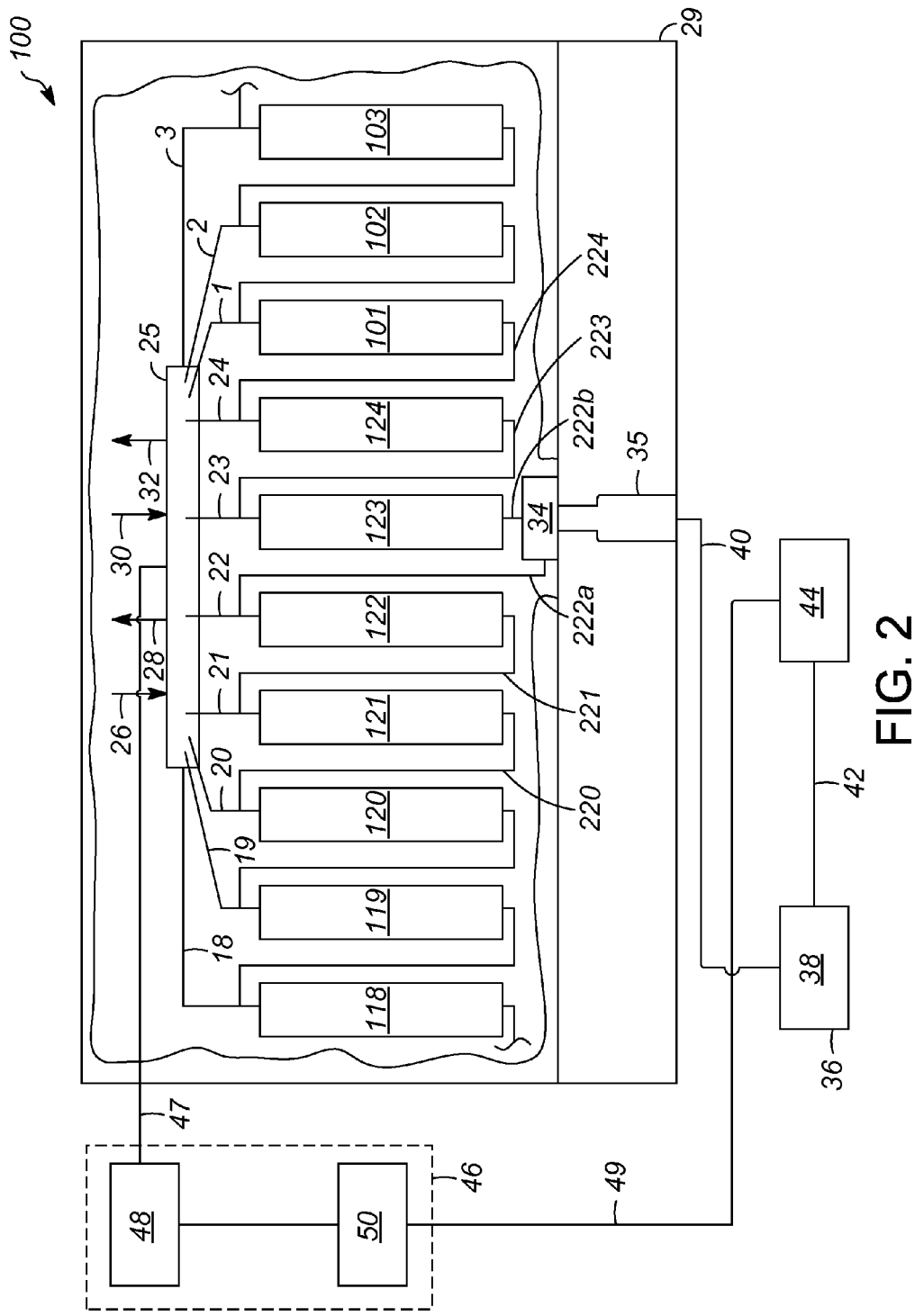
FIG. 2 schematically illustrates a tear away side view of a simulated moving bed system in accordance with an exemplary embodiment.

Referring to FIGS. 1 and 2, an exemplary embodiment of a simulated moving bed system 100 for separating para-xylene from a feed stream is provided. The system 100 includes distribution lines 1-24 for fluidly communicating liquid streams to or from the adsorbent sub-beds 101-124. All of the distribution lines 1-24 are also connected to a rotary valve 25. The rotary valve 25 is further connected to line 26 that fluidly communicates the feed to the rotary valve 25, line 28 that that fluidly communicates raffinate away from the rotary valve 25, line 30 that fluidly communicates desorbent to the rotary valve 25, and line 32 that fluidly communicates extract away from the rotary valve 25.

As illustrated, the push-around lines 201-224 conduct intermediate streams of effluent in the counterclockwise direction from the tops of corresponding adsorbent sub-beds 101-124 to the bottoms of adjacent adsorbent sub-beds 101-124. In particular, adsorbent sub-beds 122 and 123 are in direct fluid communication with each other via push-around lines 222a and 222b that fluidly communicate the intermediate stream to and from a probe holder 34. The rotary valve 25, adsorbent sub-beds 101-124, the distribution lines 1-24, push-around lines 201-224, and the probe holder 34 are arranged in a hot box 29 that provides these components a heated environment for the separation process. In an exemplary embodiment, the hot box 29 is operating at a temperature of from about 200 to about 235° C.

The probe holder 34 provides an inline sampling interface for a probe 35 of the Raman system 36 to sample the intermediate stream. In particular and as discussed in further detail below, the probe holder 34 positions the distal-most tip portion of the probe 35 in the intermediate stream for inline sampling of the intermediate stream without obstructing the stream. As illustrated, the probe holder 34 is interposed in the intermediate stream between the two adjacent adsorbent sub-beds 122 and 123. However, the probe holder 34 may be positioned interposingly in any one of the intermediate streams between any two adjacent adsorbent sub-beds 101-124. This is because each of the intermediate streams carry correspondingly distinct compositions for a particular valve position of the rotary valve 25. However, for one complete valve cycle, each of the intermediate streams will have sequentially carried the compositions corresponding to all of the relative positions of the rotary valve 25.

The Raman system 36 includes a Raman spectrophotometer 38 that is coupled to the probe 35 by a fiber optic cable 40. The Raman spectrophotometer 38 is configured to generate laser light in the visible, near infrared, or near ultraviolet range that is advanced through the fiber optic cable 40 and directed into the intermediate stream by the probe 35. In a preferred embodiment, the Raman spectrophotometer 38 generates laser light having a wavelength of about 785 nm. The probe 35 is configured to collect the scattered light from the irradiated intermediate stream as the molecules in the intermediate stream begin to relax. The scattered light is returned to the Raman spectrophotometer 38 through the fiber optic cable 40. The Raman spectrophotometer 38 is also configured to generate a spectrum of the scattered light that represents a compositional fingerprint of the intermediate stream. One such suitable Raman spectrophotometer 38 is the Kaiser Optical Raman RXN4 spectrophotometer which is manufactured by Kaiser Optical Systems Inc. located in Ann Arbor, Mich.

Figure 4B:
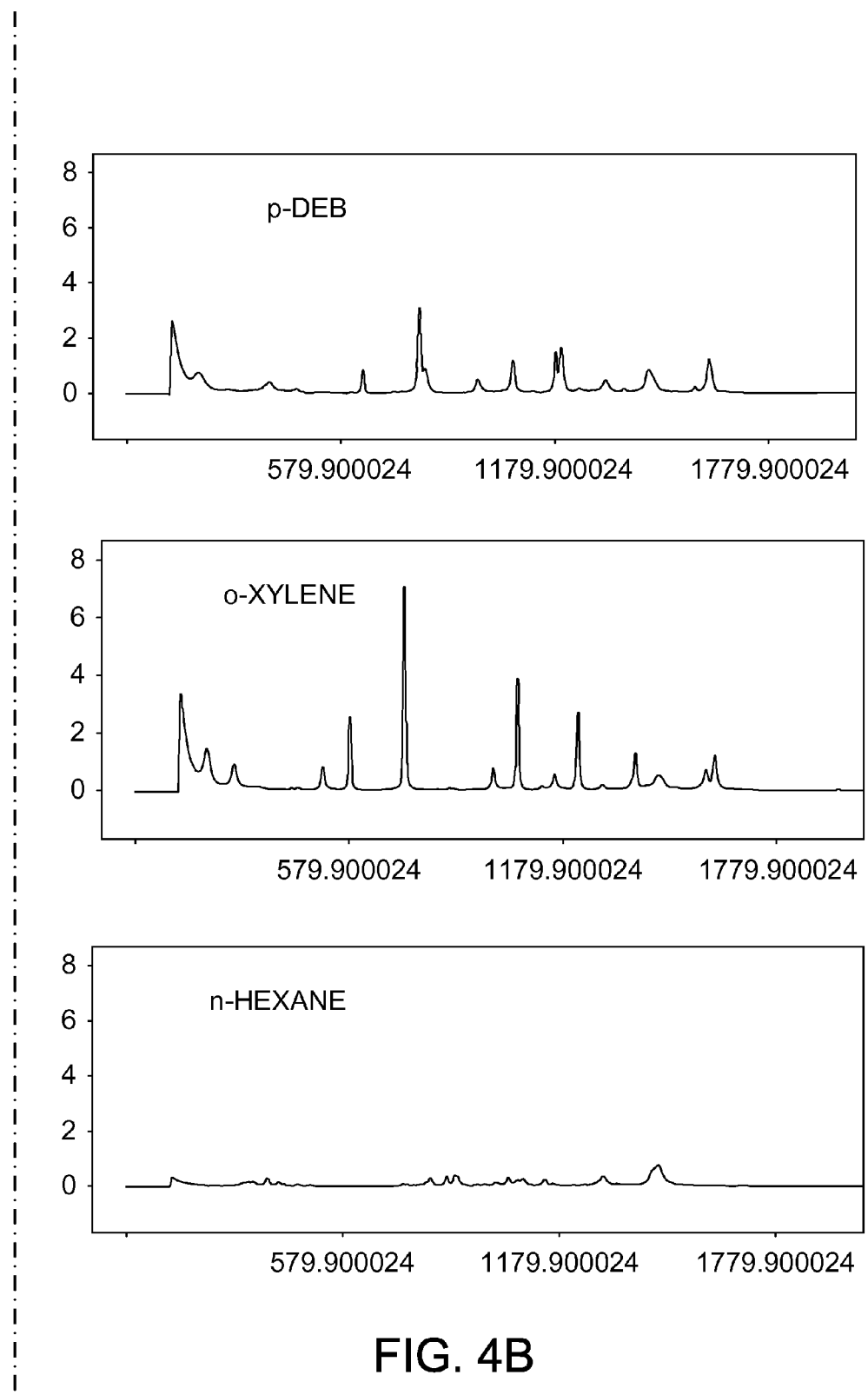

In an exemplary embodiment and as shown in FIG. 4, which illustrates six Raman spectra of the pure components of para-xylene, meta-xylene, ortho-xylene, ethylbenzene, para-diethylbenzene, and n-hexane, the Raman system 36 generates a spectrum that contains the relative intensity (Response (E+05)) on the y-axis versus the wave number (reciprocal of the wavelength in $cm^{-1}$) on the x-axis for the scattered light, which corresponds to the various molecules that make up the intermediate stream. Thus, as the rotary valve 25 rotates to each of the valve positions in a valve cycle, the compositional makeup (e.g. relative amounts of each of the components) of the intermediate stream will change accordingly. The spectrum generated via the Raman system 36 for each of the valve positions is a composite spectrum (e.g. composite of all six spectra illustrated in FIG. 4) of the components in the intermediate stream based on their relative concentrations and integrated over the composition range within the adsorbent sub-bed at that valve position. The composite spectrum includes the relative intensities over various wave number regions for each of the components that can be further analyzed as discussed below to determine the compositional makeup of the intermediate stream.

As illustrated in FIG. 2, the Raman system 36 is coupled by a data bus 42 to a computer 44. A timer-control unit 46 is coupled to the rotary valve 25 and to the computer 44 by buses 47 and 49, respectively. The timer-control unit 46 includes a timer 48 and a controller 50 cooperatively configured to define the step time for the rotary valve 25 and to generate a trigger signal to the computer 44 in response to the rotary valve 25 indexing to the next valve position.

In an exemplary embodiment, an algorithm installed in the spectrophotometer software is executed on the computer 44. The algorithm correlates the concentrations of the components in the intermediate stream to the spectrum generated by the Raman system 36. In particular, the inventors generated spectra for the six pure components of para-xylene, meta-xylene, ortho-xylene, ethylbenzene, para-diethylbenzene, and n-hexane (illustrated in FIG. 4) and mixtures of these components. From this and using selected wave number regions for each of the six components and multivariate models including partial least square analysis, the algorithm was developed to quantitatively analyze the concentrations of each of these six components in a composite spectrum for the intermediate stream.

Figure 3:
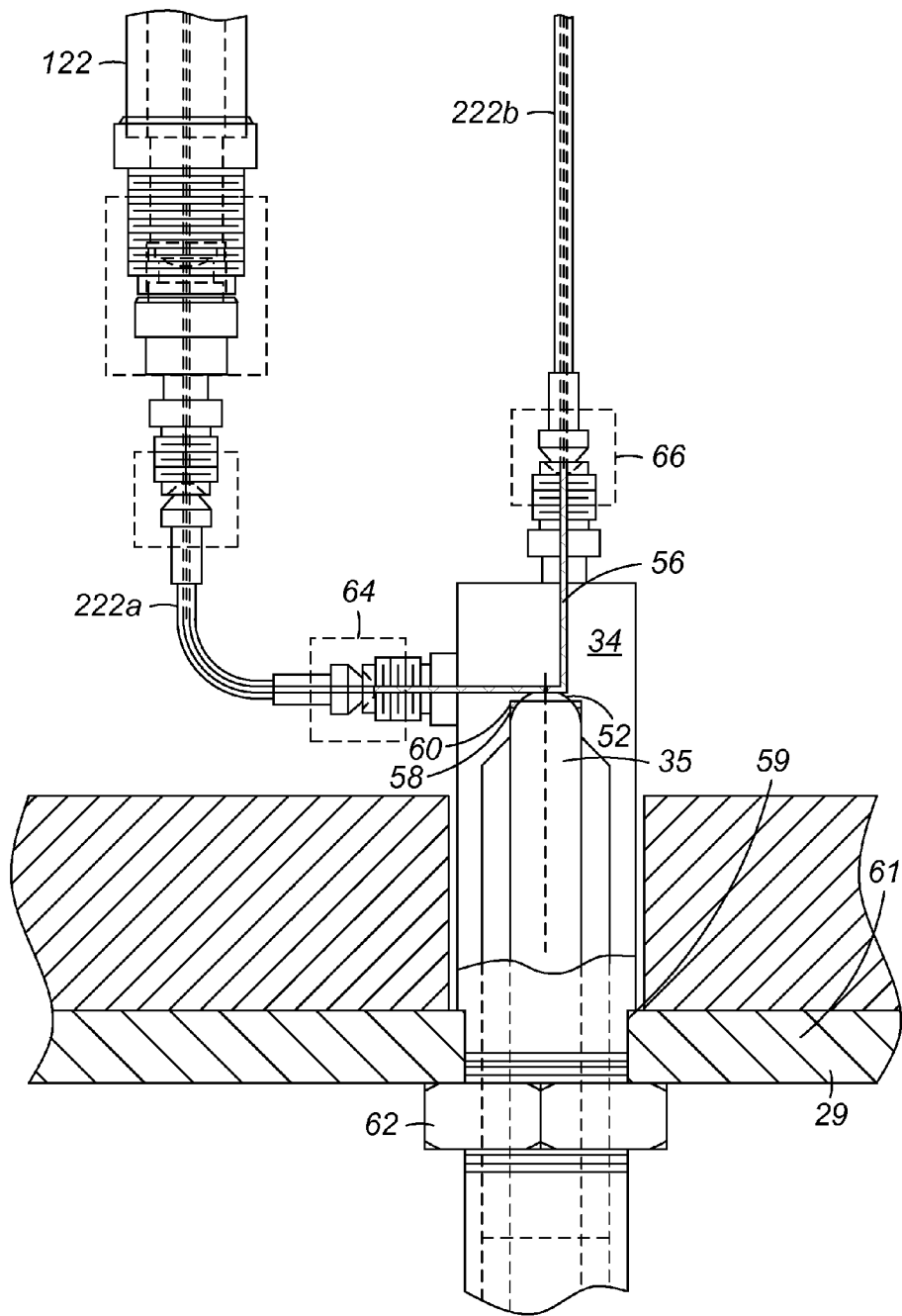
FIG. 3 is a partial side sectional view of a simulated moving bed system including a probe holder in accordance with an exemplary embodiment.

In an exemplary embodiment and with reference to FIG. 3, the probe holder 34 extends into the hot box 29 through an opening formed through the hot box wall 61 and is exposed to the heated environment. The probe holder 34 has an outer circumference step 59 formed at an intermediate portion of the probe holder 34 that interfaces with an upper surface of the hot box wall 61. A threaded fastener 62 is positioned on the probe holder 34 below the step 59 to capture the hot box wall 61 between the step 59 and the threaded fastener 62 and to secure the probe holder 34 to the hot box 29.

The probe holder 34 has a channel 56, which as illustrated is an L-shaped channel but may be shaped in any suitable configuration, formed through an upper portion of the probe holder 34 for carrying the intermediate stream. The push-around line 222a from the adsorbent sub-bed 122 is coupled to the probe holder 34 at the bottom end of the L-shaped channel 56 with a swagelock connection 64 and the push-around line 222b from the adsorbent sub-bed 123 is coupled to the probe holder 34 at the upper end of the L-shaped channel 56 with a swagelock connection 66. Thus, the adsorbent sub-beds 122 and 123 are in direct fluid communication with each other for advancing the intermediate stream via push-around lines 222a and 222b and the L-shaped channel 56 of the probe holder 34. As illustrated, the internal flow diameter of the channel 56 is substantially the same as the internal flow diameters of the push-around lines 222a and 222b so as to preferably not alter the flow volume of the intermediate stream advancing between the two adjacent adsorbent sub-beds 122 and 123. A socket 58 is formed longitudinally in the probe holder 34 and forms an opening into the lower portion of the L-shaped channel 56. The probe 35 extends through the socket 58 where the distal tip 52 of the probe 35, which contains a sapphire window for directing laser light and collecting the scattered light, extends into the L-shaped channel 56. An O-ring 60 interfaces with the upper end of the socket 58, and the probe 35 is forced against the O-ring 60 to compress the O-ring and seal the socket 58 from the intermediate stream that is being carried in the L-shaped channel 56. In a preferred embodiment, the distal tip 52 of the probe 35 is positioned in-situ with the channel 56 and the probe 35 has a laser focal point that does not impinge the internal wall of the channel 56. In one example, the probe 35 has a laser focal point of from about 0.2 to about 0.4 mm from the distal tip 52 for irradiating the intermediate stream adjacent to the distal tip 52. However, depending on the configuration and size of the separation process, the probe 35 may have a laser focal length of less than 0.2 mm, or alternatively, of up to 3 mm or greater.

In an exemplary embodiment and referring back to FIGS. 1 and 2, the system 100 performs as follows. The flow rates of each of the lines 26, 28, 30 and 32 and the step time of the rotary valve 25, via the timer-control unit 46, may be set to a predetermined or desired type. In a preferred embodiment, the step time is set to a time of from about 60 to about 90 seconds. The starting position of the rotary valve 25 is not important, but for this example, the starting position of the rotary valve 25 is such that the desorbent is directed to the adsorbent sub-bed 103 through distribution line 3, the extract is directed from the desorbent sub-bed 109 through distribution line 9, the feed is directed to the desorbent sub-bed 117 through distribution line 17, and the raffinate is directed from the desorbent sub-bed 124 through distribution line 24.

While at the starting valve position, and during the first step time, the timer-control unit 46 generates a trigger signal that is communicated via bus 49 to the computer 44 that communicates via data bus 42 to the Raman spectrophotometer 38 to begin scanning the intermediate stream between the adsorbent sub-beds 122 and 123. In a preferred embodiment, the controller 50 subdivides the step time into an initial idle time before generating the trigger signal, an analysis or profile time during which the Raman system 36 analyzes the intermediate stream and generates a spectrum, and a final idle time where the Raman spectrophotometer 38 idles and waits for the next trigger signal for the next step time. In one example, the initial idle time is from about 0.5 to about 15 seconds, more preferably from about 0.5 to about 10 seconds, and most preferably from about 0.5 to about 5 seconds, and the profile time is from about 35 to about 55 seconds. In another example, both the initial and final idle times are from about 0.5 to about 15 seconds, more preferably from about 0.5 to about 10 seconds, and most preferably from about 0.5 to about 5 seconds, and the profile time is the step time minus the initial and final idle times. In yet another example, the controller 50 generates multiple trigger signals during the profile time to direct the Raman spectrophotometer 38 to take multiple readings of the intermediate stream. It is believed that by measuring the concentrations of the components in the intermediate stream after an initial idle time, unstable or transient levels in the concentrations of the intermediate stream components due to the rotary valve 25 changing positions are avoided.

After the Raman system 36 is directed to begin scanning, the concentrations of the para-xylene and one or more other components, e.g. one or more other $C_8$ aromatics and other components, in the intermediate stream are measured using the probe 35, which is positioned for inline sampling via the probe holder 34, the fiber optic cable 40 and the Raman spectrophotometer 38. First, the Raman spectrophotometer 38 acquires a dark scan, which essentially determines the number of counts the CCD array of the Raman spectrophotometer 38 produces when the Raman spectrophotometer's shutter is closed and the detector is seeing nothing. This step, however, does not need to be preformed for each scan or even in response to the trigger signal, and therefore, can be performed occasionally and/or during a time other than the profile time. Then, the Raman system 36 irradiates the intermediate stream with the laser light and collects the scattered light. The Raman spectrophotometer 38 generates a spectrum, preferably through a series of acquisition and accumulation steps of irradiating the stream and collecting the scattered light that is then electronically communicated via the data bus 42 to the computer 44. The computer 44, using the algorithm, analyzes the spectrum to determine the concentrations for each of the components achieved during the rotary valve 25 being in the starting valve position, and the values are stored in the computer 44.

Figure 5:
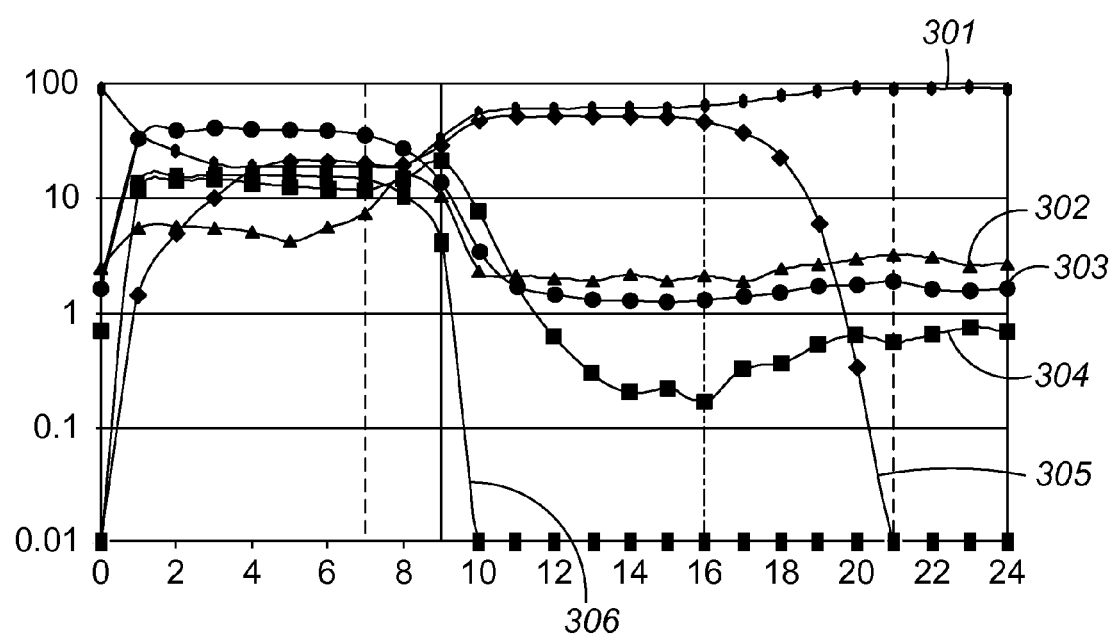
FIG. 5 is a graphical representation of a pump-around profile of a simulated moving bed system in accordance with an exemplary embodiment.

After the completion of the first step time, the entire process may be repeated again for each of the valve positions of the rotary valve 25 to determine the concentrations of each of the components for each of the valve positions. Referring to FIG. 5, the concentrations for the components, e.g., para-xylene 305, meta-xylene 303, ortho-xylene 306, ethylbenzene 304, para-diethylbenzene 301, and n-hexane 302, at each of the 24 valve positions can be graphically represented as weight percent, (y-axis), versus valve position, (x-axis). As illustrated, the valve positions on the x-axis represent the raffinate out position (ROP), which in this example, ROP valve position #1 corresponds to the raffinate being conducted out of the desorbent sub-bed 124 via distribution line 24.

Accordingly, simulated moving bed systems for separating para-xylene from a feed stream hydrocarbon mixture and processes for determining a pump-around profile of the simulated moving bed systems have been described. The various embodiments comprise a plurality of adsorbent sub-beds in fluid communication with each other and with a rotary valve for separating para-xylene from a feed stream comprising para-xylene and one or more other $C_8$ aromatics. The Raman system includes a probe operatively coupled to a Raman spectrophotometer, for example by a fiber optic cable or cables. Without interrupting the process stream for the simulated moving bed system, the probe is positioned for inline sampling of an intermediate stream that is between two of the adsorbent sub-beds that are in direct fluid communication with each other. Preferably, a computer operatively interfaces with the Raman spectrophotometer, and a controller operatively interfaces with the rotary valve and the computer. In response to the rotary valve rotating an index to a particular valve position to reposition the feed stream, the controller generates a signal to the computer which triggers the Raman spectrophotometer to begin analyzing the intermediate stream. A short idle time between when the rotary valve indexes and the Raman system begins analyzing the intermediate stream is preferably used to ensure a more accurate determination of the concentration of the intermediate stream achieved during the rotary valve being in a particular valve position. The intermediate stream is irradiated with laser light directed from the probe and emits light that is collected by the probe. The Raman system generates a spectrum of the scattered light. Because the intermediate stream contains various amounts of para-xylene and one or more other components, in one approach one or more other $C_8$ aromatics, from the feed stream based on the valve position, the spectrum is a composite of all of these components. An algorithm that correlates the concentrations of the components to the spectrum is preferably used to analyze the spectrum and to calculate the concentrations of the components. The concentration of each of the components may then be graphically represented for that particular valve position. In an exemplary embodiment, the Raman spectrophotometer in combination with the controller, computer and algorithm are used to automatically generate and graphically represent the concentrations of each of the components in the intermediate stream for each valve position for a full valve cycle to generate a pump-around profile. This process may run continuously to provide ongoing pump-around profiles of the simulated moving bed system. Thus, the pump-around profiles of the system can be provided with rapid and frequent analytical results. Furthermore, the process can be fully automated requiring little or no maintenance and essentially no operator time and labor for generating the pump-around profiles. Moreover, the probe is positioned for inline sampling of the intermediate stream to provide information similar to the manual sampling procedure but without increasing the process stream volume or disrupting production.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

The invention claimed is:

1. A process for determining a pump-around profile of a simulated moving bed system having a plurality of adsorbent sub-beds in fluid communication with each other and with a rotary valve for separating one or more preferentially adsorbed components from a feed stream comprising the preferentially adsorbed component and one or more other non-preferentially adsorbed components, wherein the adsorbent sub-beds and the rotary valve are disposed in a hot box, the process comprising the steps of:
   rotating the rotary valve to a first valve position to direct the feed stream to a first adsorbent sub-bed of the plurality of adsorbent sub-beds;
   irradiating an intermediate stream between two of the adsorbent sub-beds in direct fluid communication with each other with laser light that is directed from a probe of a Raman system positioned for inline sampling of the intermediate stream;
   collecting scattered light from the irradiated intermediate stream with the probe;
   generating a spectrum of the scattered light with the Raman system to assess concentrations of the preferentially adsorbed component and one or more other components in the intermediate stream;
   holding the probe such that at least a tip portion of the probe is positioned in the hot box in-situ with the intermediate stream;
   operating the hot box at a temperature of from about 200 to about 235° C.; and,
   exposing the tip portion of the probe to the temperature in the hot box.

2. The process of claim 1, wherein the feed stream comprises $C_8$ aromatics and the preferentially adsorbed component comprises para-xylene.

3. The process of claim 1, wherein the feed stream comprises $C_8$ aromatics and the preferentially adsorbed component comprises meta-xylene.

4. The process according to claim 1, wherein the step of rotating the rotary valve includes rotating the rotary valve to a plurality of valve positions that each direct the feed stream to a different one of the plurality of the adsorbent sub-beds, and the steps of irradiating, collecting and generating are repeated for each of the plurality of valve positions to assess the concentrations of the preferentially adsorbed component and the one or more other components in the intermediate stream produced during the rotary valve being in each of the valve positions.

5. The process according to claim 4, wherein a number of the plurality of valve positions corresponds to a number of the plurality of adsorbent sub-beds, wherein the number of the plurality of valve positions is 24 defining a full valve cycle, and wherein the step of rotating the rotary valve includes rotating the rotary valve for the full valve cycle, and the steps of irradiating, collecting and generating are repeated until the full valve cycle is completed.

6. The process according to claim 4, wherein the step of rotating the rotary valve includes maintaining the rotary valve in each of the plurality of valve positions for a hold period before rotating the rotary valve to another of the plurality of valve positions.

7. The process according to claim 6, where the steps of irradiating, collecting and generating occur during the hold period.

8. The process according to claim 7, wherein the hold period is subdivided into first and second idle times and a profile time that occurs between the first and second idle times, and the steps of irradiating, collecting and generating occur during the profile time.

9. The process according to claim 8, wherein the first idle time is from about 0.5 to about 15 seconds, and the profile time is from about 35 to about 55 seconds, and the second idle time is the remaining time of the hold period after the first idle and profile times.

10. The process according to claim 8, wherein the first and second idle times are each from about 0.5 to about 15 seconds, and the profile time is the hold time less the first and second idle times.

11. The process according to claim 8, wherein the step of generating the spectrum includes the Raman system taking multiple scans of the intermediate stream during the profile time.

12. The process according to claim 1, wherein the probe has a distal tip and a laser focal point of about 0.4 mm or less from the distal tip, and the step of irradiating the intermediate stream includes irradiating the intermediate stream with the laser light at a distance of about 0.2 to about 0.4 mm from the distal tip.

13. The process according to claim 1, wherein the step of irradiating includes irradiating the intermediate stream between two of the adsorbent sub-beds that are immediately adjacent to each other.

14. The process according to claim 1, further comprising the step of calculating the concentrations according to an algorithm correlating the concentrations to the spectrum.

* * * * *